United States Patent
Obara

(10) Patent No.: US 6,849,729 B2
(45) Date of Patent: Feb. 1, 2005

(54) LOW-SUBSTITUTED CELLULOSE ETHER POWDER AND PRODUCTION PROCESS THEREOF

(75) Inventor: Sakae Obara, Niigata-ken (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 0 days.

(21) Appl. No.: 10/375,444

(22) Filed: Feb. 27, 2003

(65) Prior Publication Data
US 2003/0166918 A1 Sep. 4, 2003

(30) Foreign Application Priority Data
Mar. 4, 2002 (JP) ........................ 2002-056992

(51) Int. Cl.$^7$ ................... C08B 11/00; C08B 11/20; C08B 11/02; C07H 1/00
(52) U.S. Cl. ................ 536/84; 536/85; 536/86; 536/89; 536/95; 536/96; 536/99; 536/100; 536/124
(58) Field of Search .............. 536/84, 85, 86, 536/89, 95, 96, 99, 100, 124

(56) References Cited

U.S. PATENT DOCUMENTS

| 4,091,205 A | 5/1978 | Onda et al. ............. 536/85 |
| 4,258,179 A | 3/1981 | Kawata et al. .......... 536/95 |

FOREIGN PATENT DOCUMENTS

| EP | 1120427 | 1/2001 |
| GB | 616304 | 5/1946 |
| JP | 52143673 | 11/1977 |
| JP | 62310733 | 12/1987 |
| JP | 09110420 | 4/1997 |

OTHER PUBLICATIONS

English Abstract of Japanese Patent Publication (JP–B) No. 62–61041/'87.

English Abstract of Japanese Patent Publication (JP–B) No. 6–49768/'94.

Primary Examiner—Johann Richter
Assistant Examiner—Everett White
(74) Attorney, Agent, or Firm—Myers Bigel Sibley & Sajovec, P.A.

(57) ABSTRACT

Provided is a cellulose polymer having a water retention property, and good feeling upon use when applied to the skin and being suitably used as a carrier. More specifically, provided is a low-substituted cellulose ether powder comprising primary particles wherein at least 95% by weight of the primary particles have an aspect ratio of 1.0 to 1.5. Also provided is a production process of a low-substituted cellulose ether powder having a molar substitution degree of 0.05 to 1.0, comprising, during or after the addition of an acid to an alkali solution of low-substituted cellulose ether to neutralize the solution, triturating a resulting mixture; and spray-drying a resulting dispersion. Further provided is a production process of a low-substituted cellulose ether powder having a molar substitution degree of 0.05 to 1.0, comprising shear-triturating a low-substituted cellulose ether powder in water so as to swell-disperse the powder and spray-drying a resulting dispersion.

5 Claims, 3 Drawing Sheets

LOW-SUBSTITUTED CELLULOSE ETHER POWDER AND PRODUCTION PROCESS THEREOF

RELATED APPLICATION

This application claims priority from Japanese Patent Application No. 2002-056992 filed Mar. 4, 2002, the disclosure of which is incorporated by reference herein in its entirety.

BACKGROUND OF THE INVENTION

1. Field of the Invention

The present invention relates to a low-substituted cellulose ether powder used preferably as a dispersion stabilizer, a viscosity adjustment agent or the like of foods, pharmaceuticals, cosmetics, aqueous coatings, inks, starches and the like; and a production process thereof.

2. Description of the Related Art

Cellulose polymers have made a great contribution to the above-described fields. For example, crystalline cellulose, cellulose powder or water soluble cellulose derivatives have been used widely. Japanese Patent Publications (JP-B) Nos. 56-54292/1981 (U.S. Pat. No. 4,258,179), 62-61041/1987 and 6-49768/1994 disclose production processes of an aqueous gel comprising steps of dispersing a low-substituted cellulose ether powder in water and shear-triturating the resulting dispersion.

SUMMARY OF THE INVENTION

In the above-described industrial fields, cellulose polymers are required to have such performances as easy handling, good stability, viscosity and a shape-retaining property adequate for each application, and good feeling when used. Crystalline cellulose has such performances that it is widely used. However, it is slightly insufficient in water-retaining property. The low-substituted cellulose ethers of prior art are in fibrous form so that feeling upon their application to the skin is not good. In addition, because none of the low-substituted cellulose ethers is substantially spherical in a stage of primary particles, it is not suitable for a carrier. An object of the present invention is to provide cellulose polymer which can overcome these problems.

As a result of extensive investigation, the present inventor has found a substance capable of overcoming the above-described problems and completed the present invention. In one aspect of the present invention, there is thus provided a low-substituted cellulose ether powder comprising primary particles, wherein at least 95% by weight of the primary particles have an aspect ratio of 1.0 to 1.5. In another aspect of the present invention, there is also provided a production process of a low-substituted cellulose ether powder having a molar substitution degree of 0.05 to 1.0, comprising, during or after addition of an acid to an alkaline solution of a low-substituted cellulose ether to neutralize the solution, shear-triturating the resulting mixture and then spray-drying the resulting dispersion. In a further aspect of the present invention, there is also provided a production process of a low-substituted cellulose ether powder having a molar substitution degree of 0.05 to 1.0, comprising shear-triturating a low-substituted cellulose ether powder so as to swell-disperse the powder in water, and spray-drying the resulting dispersion.

The low-substituted cellulose ether powder according to the present invention is superior in form of particles to that of the prior art. When it is added to foods, pharmaceuticals or cosmetics in the paste or gel form, or aqueous coatings, inks, starches or the like, it exhibits an excellent water-retaining, dispersion-stabilizing and/or thickening effect.

DETAILED DESCRIPTION OF THE PREFERRED EMBODIMENTS

Figure 1:
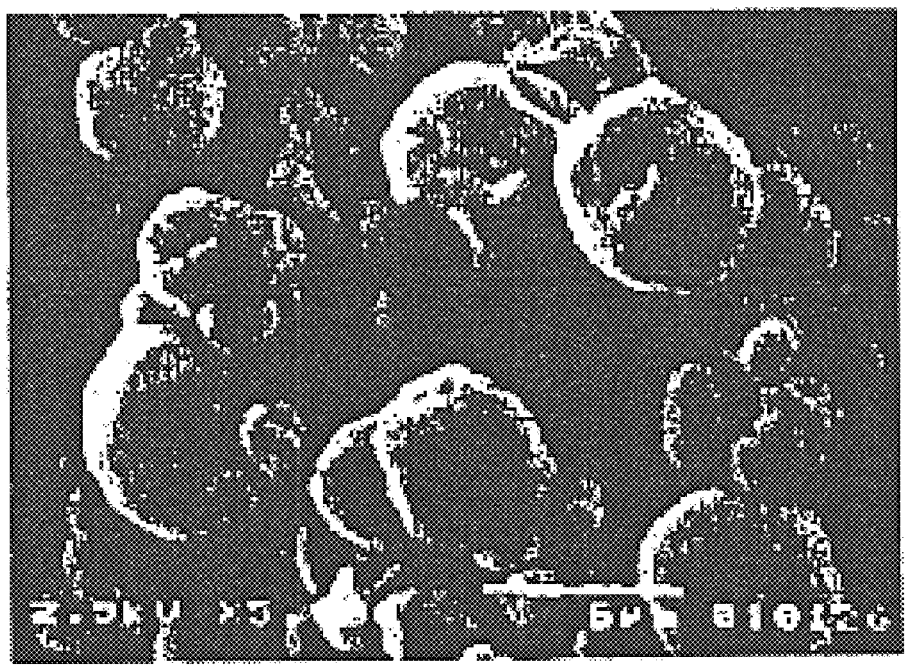
FIG. 1 is an SEM photograph (5,000×) of a low-substituted hydroxypropyl cellulose powder prepared in Example 1.

The present invention will hereinafter be described more specifically.

The low-substituted cellulose ether of the present invention is soluble not in water but in an alkaline solution. In general, cellulose is not water soluble, but substitution of a hydrogen atom of a hydroxyl group on a glucose ring constituting the cellulose with an alkyl or hydroxyalkyl group may add water solubility thereto, depending on the degree of substitution. The cellulose having a low degree of substitution is not soluble in water, but instead, tends to be soluble in an alkaline solution. In many cases, when a low-substituted cellulose powder is dispersed in water, a portion thereof may be swelled with water. Cellulose having a high degree of substitution becomes soluble in water, but loses solubility in an alkaline solution. An aqueous gel of the present invention cannot be obtained by using such a water soluble cellulose ether.

The low-substituted cellulose ether mainly used in the present invention has preferably a molar substitution degree of 0.05 to 1.0. A desirable wt % range (the numeral in parentheses below is a molar substitution degree) of the substituent will be described below. It is to be noted that the molar substitution degree can be measured with reference to the Japanese Pharmacopoeia.

Low-substituted methyl cellulose: 3 to 15% by weight (0.16 to 0.85) of a methoxyl group Low-substituted hydroxyethyl cellulose: 3 to 15% by weight (0.08 to 0.45) of a hydroxyethoxyl group Low-substituted hydroxypropyl cellulose: 4 to 20% by weight (0.09 to 0.51) of a hydroxypropyl group Low-substituted hydroxypropylmethyl cellulose: 3 to 12% by weight of a methoxyl group and 4 to 20% by weight of a hydroxypropyl group (0.25 to 1.0 in total of both substituents)

Such low-substituted cellulose ethers are insoluble in water but soluble in an alkaline solution. In addition, it absorbs water and swells therewith. Low-substituted hydroxypropyl cellulose is one of the typical examples and now commercially available as a trade name of Low-Substituted Hydroxypropyl Cellulose from Shin-Etsu Chemical Co., Ltd. It is listed in the Japanese Pharmacopoeia and generally used as a disintegrant to be incorporated in tablets particularly in the field of pharmaceutical materials.

Known preparation processes of these low-substituted cellulose ethers are described, for example, in Japanese Patent Publication (JP-B) No. 57-53100/1982 (U.S. Pat. No. 4,091,205). Firstly, preparation of an alkali cellulose is necessary. It may be prepared, for example, by immersing a sheet-like pulp, which is a starting material, in an aqueous alkaline solution such as sodium hydroxide; by mixing pulverized pulp with an alkaline solution; or by dispersing pulp powder in an organic solvent and then adding an alkali to the resulting dispersion. The alkali cellulose thus obtained may be then charged in a reactor and after addition thereto of an etherifying agent such as propylene oxide or ethylene oxide, the mixture may be heated to cause reaction, whereby the corresponding cellulose ether is obtained. After the reaction is over, the crude cellulose ether obtained may be transferred to another tank, in which the alkali may be neutralized with an acid. The resulting solid may be then washed, dried and pulverized to yield a finished product in the powder form. Alternatively, it may be also obtained by dissolving the crude cellulose ether just after the reaction in water completely or partially, neutralizing the resulting solution, and collecting the polymer precipitated, washing, drying and then pulverizing the polymer.

On the other hand, according to the production process of the present invention, low-substituted cellulose ether is dissolved once in an aqueous alkaline solution; and during or after neutralization, the solution is shear-triturated and the dispersion thus obtained is spray dried. A similar result may be obtained for the low-substituted cellulose ether powder obtained as the finished product in the above-described manner being dissolved in an aqueous alkaline solution or for the crude cellulose ether being dissolved in water just after the reaction. In the latter case, since the crude cellulose ether contains an alkali, water may be used alone as a solvent for dissolving the ether, but an alkali may be sometimes added further in order to ensure complete dissolution of the cellulose ether. Either method is embraced in the present invention.

Examples of the alkali used for dissolving the ether include potassium hydroxide and sodium hydroxide. Its concentration may be determined in each case because of dependency on the substituent or substitution degree of the cellulose ether to be employed. It may be usually 2 to 25% by weight, especially 3 to 15% by weight. As a typical example, low-substituted hydroxypropyl cellulose having a molar substitution degree of 0.2 is dissolved in 10% by weight of sodium hydroxide. The solution thus obtained may be clear in some cases but not completely clear in some cases, depending on a difference in the distribution of the substituent. In the latter cases, an apparent increase of viscosity is considered to mean that the ether is dissolved in an alkali.

The alkaline solution may be neutralized with an equivalent amount of hydrochloric acid, sulfuric acid, acetic acid or the like. The alkaline solution may be shear-triturated in a shear-triturator while adding an acid in portions to proceed with neutralization, or may be neutralized with an equivalent amount of an acid in advance and then a solution containing the precipitated polymer may be shear-triturated.

Shear-trituration of an alkaline solution or a neutralized solution of cellulose ether having a proper concentration may be carried out, preferably in an emulsify-dispersing machine. No particular limitation is placed on the emulsify-dispersing machine. The examples include an vibration ball mill, a colloid mill, a homomixer, and homogenizers such as a propeller homogenizer, a high pressure homogenizer and a ultrasonic homogenizer. Among them, the homogenizers are preferred. High pressure homogenizers for spraying a fluid through openings of valve under high pressure (for example, "Homogenizer" manufactured by Sanwa Machine Co., Ltd., "Ultimaizer System" manufactured by Sugino Machine Co., Ltd., "Microfluidizer" manufactured by Mizuho Kogyo Co., Ltd., and a high pressure homogenizer manufactured by Gaulin Co., Ltd.), and a ultrasonic homogenizer utilizing oscillation of an ultrasonic wave (for example, "Ultrasonic Homogenizer" manufactured by Nippon Seiki Co., Ltd.) are preferred for the preparation of a uniform aqueous dispersion.

Trituration of the alkaline solution may be carried out while gradually adding an acid such as hydrochloric acid, sulfuric acid or acetic acid. The shear-trituration condition is not particularly limited, but 3,000 to 15,000 rpm, particularly 10,000 to 15,000 rpm is preferred when a propeller homogenizer is employed. A pressure 00 to 2,000 kg/cm$^2$, particularly 200 to 2,000 kg/cm$^2$ is preferred when a high pressure homogenizer is employed.

The cellulose ether concentration in the solution upon trituration may be preferably 0.01 to 20% by weight, particularly 0.1 to 10% by weight. Concentrations higher than the above-described range may cause an excessive rise in viscosity, which may disturb smooth trituration.

A salt formed by the neutralization exists in the dispersion thus prepared. If necessary, it may be removed by means of centrifugal separation, dialysis or the like. It should be noted that the dispersion of the present invention embraces a gel.

Alternatively, without dissolving the low-substituted cellulose ether in an alkali, it can be swelled and dispersed in water, followed by shear-trituration, preferably using an emulsifying disperser.

The powder may be obtained by ordinarily employed spray-drying. The spray-drying may be performed at 20 to 150° C. by a spray-drier. The powder thus obtained has primary particles in a substantially spherical shape wherein at least 95% by weight of the primary particles have an aspect ratio (a ratio of a major axis to a minor axis of the particle) of 1.0 to 1.5. Different from the conventional one, the powder does not contain fibrous particles. Spherical granules obtained by wet granulation of low-substituted cellulose ether containing fibrous particles are not regarded as primary particles, being different from that of the present invention. The aspect ratio is expressed by a ratio of a major diameter to a minor diameter of the particle based on a scanning electron microscopic (SEM) observation. Particles having an aspect ratio outside the above-described range may be insufficient in feeling upon use when applied to the skin.

The average particle size of the low-substituted cellulose ether of the present invention may be usually 1 mm or less, preferably 100 µm or less, more preferably 10 µm or less when measured by the method (limited only to a dry method) such as a sieving method, a laser diffraction method or visual method through a microscope. Although no particular limitation is placed on the lowest limit, it may be usually 0.1 µm or greater. The particle size may be controlled by varying on the condition such as shear-triturating force applied for the preparation of the dispersion or a concentration of the dissolved polymer.

Specific Examples and Comparative Examples will next be described. However, it should not be construed that the present invention is limited to or by them.

EXAMPLE 1

In 425 g of a 6.3 wt % aqueous NaOH solution was dissolved 7.5 g of low-substituted hydroxypropyl cellulose powder (produced by Shin-Etsu Chemical Co., Ltd., molar substitution degree of 0.2, average particle size of 100 µm). While shear-triturating the resulting solution in a homogenizer ("AM-10" manufactured by Nippon Seiki Co., Ltd.) at 5,000 rpm, an equivalent amount of acetic acid to the amount required for neutralization was added dropwise for 5 minutes from a small opening of a container. After the neutralization, the shear-trituration was continued for further 10 minutes at 10,000 rpm. The gel thus obtained was subjected to centrifugal separation at 10,000 rpm. The supernatant was discarded, while the precipitate was dispersed again after pure water was added thereto so as to form a solid concentration of 2% by weight. The dispersion was spray-dried at intake temperature of 120° C. using a spray dryer ("Minispray" produced by Pulvis Co., Ltd.) whereby the corresponding powder was obtained.

Figure 2:
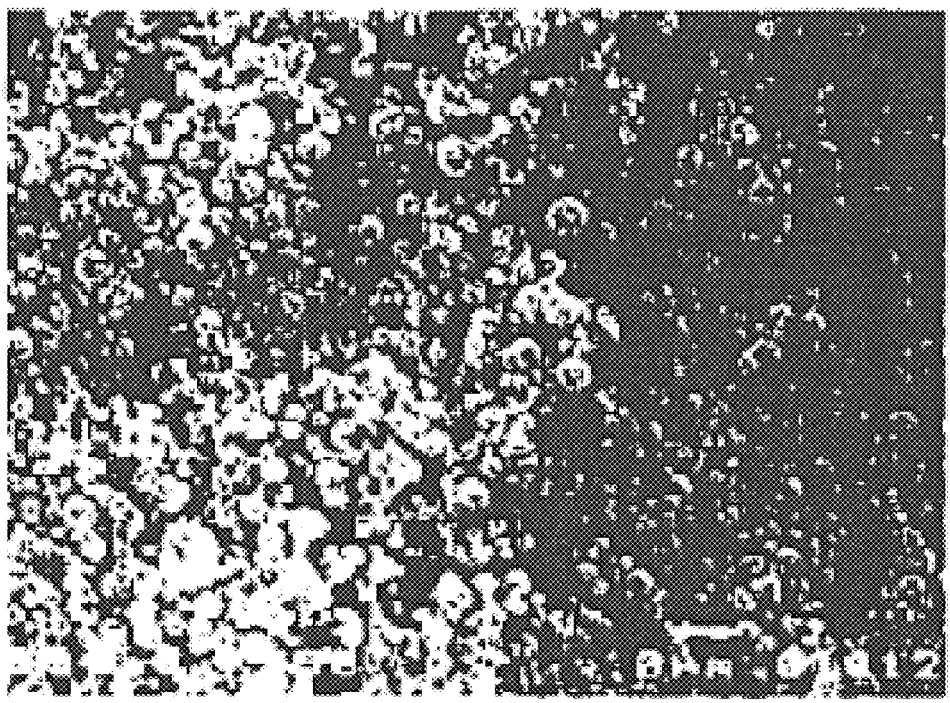
FIG. 2 is an SEM photograph (250×) of a low-substituted hydroxypropyl cellulose powder prepared in Example 1.

The powder was observed through an electron microscope. As a result, the primary particles were spherical and at least 95% by weight of the particles had an aspect ratio of 1.1 (refer to FIGS. 1 and 2). An average particle size was 2 μm as determined based on photographs.

EXAMPLE 2

A pulp sheet was immersed in 49% by weight sodium hydroxide solution and the alkali cellulose thus obtained was cut into chips of 1 cm×1 cm. The resulting chips were placed in a reactor, and 11 g of propylene oxide was added thereto. The reactor was under nitrogen atmosphere and then hermetically sealed. While stirring, heating was conducted at 60° C. for 5 hours. A small amount of the reaction mixture was sampled. After neutralization, washing and drying, its molar substitution degree was measured to be 0.2. Aside from it, 7 g of the reaction product was dissolved in 400 g of water. While turning the solution at 5,000 rpm in a homogenizer similar to that used above, the solution was neutralized gradually by adding acetic acid for 5 minutes from a small opening of the chamber. After the neutralization, shear-trituration was continued for further 5 minutes at 1,000 rpm. The aqueous gel thus obtained was subjected to centrifugal separation for 10 minutes at 10,000 rpm. After removal of the supernatant, 350 mg of pure water was added to the resulting mixture and re-dispersed. The supernatant was removed after centrifugal separation. A similar operation was repeated again to purify the gel. Water was then added to adjust the concentration of the cellulose ether to 3% by weight. The dispersion thus obtained was spray-dried using a spray drier ("Minispray" manufactured by Pulvis Co., Ltd.) at intake temperature of 120° C., whereby the corresponding powder was obtained.

As a result of observation of the powder through an electron microscope, the primary particles were in the spherical form and at least 95% by weight of the particles had an aspect ratio of 1.1. The average particle size determined based on photographs was 3 μm.

EXAMPLES 3 TO 5

In a similar manner to Example 1 except for use of low-substituted methyl cellulose (molar substitution degree of 0.28), low-substituted hydroxypropylmethyl cellulose (molar substitution degree with methoxy group of 0.13 and with hydroxypropoxyl group of 0.18) and low-substituted hydroxyethyl cellulose (molar substitution degree of 0.2) in the place of the low-substituted hydroxypropyl cellulose, the corresponding powders were prepared. As a result of the observation of the powders through an electron microscope, the primary particles were all in the spherical form. Their aspect ratios and average particle sizes as determined from photographs are shown in Table 1.

TABLE 1

|  | Aspect ratio | Average particle size (μm) |
|---|---|---|
| Low-substituted methyl cellulose | 1.4 | 900 |
| Low-substituted hydroxypropylmethyl cellulose | 1.3 | 5 |
| Low-substituted hydroxyethyl cellulose | 1.1 | 5 |

Comparative Example

Figure 3:
FIG. 3 is an SEM photograph (350×) of a commercially available low-substituted hydroxypropyl cellulose powder ("LH-31") used in Comparative Example 1.

Eight parts by weight of the powder obtained in Example 1 was dispersed in 92 parts by weight of water whereby a translucent gel having a thixotropic viscosity was obtained. When commercially available low-substituted hydroxypropyl cellulose powder ("LH-31" produced by Shin-Etsu Chemical Co., Ltd., molar substitution degree of 0.2, fibrous particles, average particle size of 17 μm, refer to FIG. 3) was dispersed in water similarly, a turbid gel was obtained. It was inferior in smoothness and touch-feeling to the skin to the gel of Example 1.

What is claimed is:

1. A low-substituted cellulose ether powder having a molar substitution degree of 0.05 to 1.0, comprising primary particles wherein at least 95% by weight of the primary particles have an aspect ratio of 1.0 to 1.5.

2. A low-substituted cellulose ether powder according to claim 1 having an average particle size of 1 mm or less.

3. A producing process of a low-substituted cellulose ether powder having a molar substitution degree of 0.05 to 1.0, comprising:

neutralizing and alkaline solution of a low substituted cellulose ether with an acid to produce a resulting mixture;

shear-triturating the resulting mixture, either during or after the acid is added to the alkaline solution; and then spray-drying the resulting dispersion.

4. A producing process of a low-substituted cellulose ether powder having a molar substitution degree of 0.05 to 1.0 and an aspect ratio of about 1.0 to 1.5, comprising:

shear-triturating a low-substituted cellulose ether powder in water so as to swell-disperse the powder; and spray-drying the resulting dispersion.

5. The process of claim 3, wherein the low-substituted ether powder comprises a low-substituted ether powder having an aspect ratio of about 1.0 to 1.5.

* * * * *